(12) United States Patent
Strong

(10) Patent No.: US 10,591,477 B2
(45) Date of Patent: Mar. 17, 2020

(54) LATERAL FLOW DEVICE AND METHOD OF USE

(71) Applicant: Bio-Rad Laboratories, Inc., Hercules, CA (US)

(72) Inventor: William Strong, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 197 days.

(21) Appl. No.: 15/656,780

(22) Filed: Jul. 21, 2017

(65) Prior Publication Data

US 2018/0024129 A1 Jan. 25, 2018

Related U.S. Application Data

(60) Provisional application No. 62/366,496, filed on Jul. 25, 2016.

(51) Int. Cl.
| | |
|---|---|
| *G01N 33/558* | (2006.01) |
| *G01N 33/52* | (2006.01) |
| *G01N 33/543* | (2006.01) |

(52) U.S. Cl.
CPC .... *G01N 33/558* (2013.01); *C12Y 102/01012* (2013.01); *C12Y 204/0203* (2013.01); *C12Y 207/11026* (2013.01); *C12Y 306/05002* (2013.01); *G01N 33/525* (2013.01); *G01N 33/54386* (2013.01); *G01N 2333/47* (2013.01); *G01N 2333/90203* (2013.01); *G01N 2333/912* (2013.01); *G01N 2333/914* (2013.01); *G01N 2333/91142* (2013.01)

(58) Field of Classification Search
CPC .................................................. G01N 33/525

USPC ........ 422/401, 420, 421, 425, 426; 436/169, 436/170, 514

See application file for complete search history.

(56) References Cited

U.S. PATENT DOCUMENTS

| | | | |
|---|---|---|---|
| 4,248,829 A * | 2/1981 | Kitajima | G01N 33/525 |
| | | | 422/423 |
| 4,981,786 A | 1/1991 | Dafforn et al. | |
| 5,198,193 A | 3/1993 | Bunce et al. | |
| 6,641,517 B2 | 11/2003 | Anderson | |
| 7,456,025 B2 | 11/2008 | Mao et al. | |
| 8,507,260 B2 | 8/2013 | Alajem et al. | |
| 9,101,927 B2 | 8/2015 | Alajem et al. | |
| 9,671,402 B2 | 6/2017 | McKee | |
| 2003/0032196 A1* | 2/2003 | Zhou | G01N 33/525 |
| | | | 436/169 |
| 2006/0068500 A1 | 3/2006 | Wei et al. | |
| 2006/0141469 A1 | 6/2006 | Rossier et al. | |

(Continued)

FOREIGN PATENT DOCUMENTS

| | | |
|---|---|---|
| EP | 1 044 372 B1 | 9/2003 |
| WO | WO 2006/080021 A2 | 8/2006 |
| WO | WO 2013/095729 A1 | 6/2013 |

OTHER PUBLICATIONS

U.S. Appl. No. 15/388,778, filed Dec. 22, 2016, Bio-Rad Laboratories, Inc.

(Continued)

*Primary Examiner* — Christopher L Chin
(74) *Attorney, Agent, or Firm* — Kilpatrick Townsend and Stockton LLP

(57) ABSTRACT

Lateral flow devices, methods and kits for performing lateral flow western blot assays are provided.

25 Claims, 9 Drawing Sheets

(56) References Cited

U.S. PATENT DOCUMENTS

2011/0189792 A1 8/2011 Reinhartz et al.
2014/0294697 A1 10/2014 Gargir et al.
2016/0038935 A1 2/2016 Alajem et al.

OTHER PUBLICATIONS

The International Search Report dated Oct. 12, 2017 in PCT/US2017/043323, filed Jul. 21, 2017.

\* cited by examiner

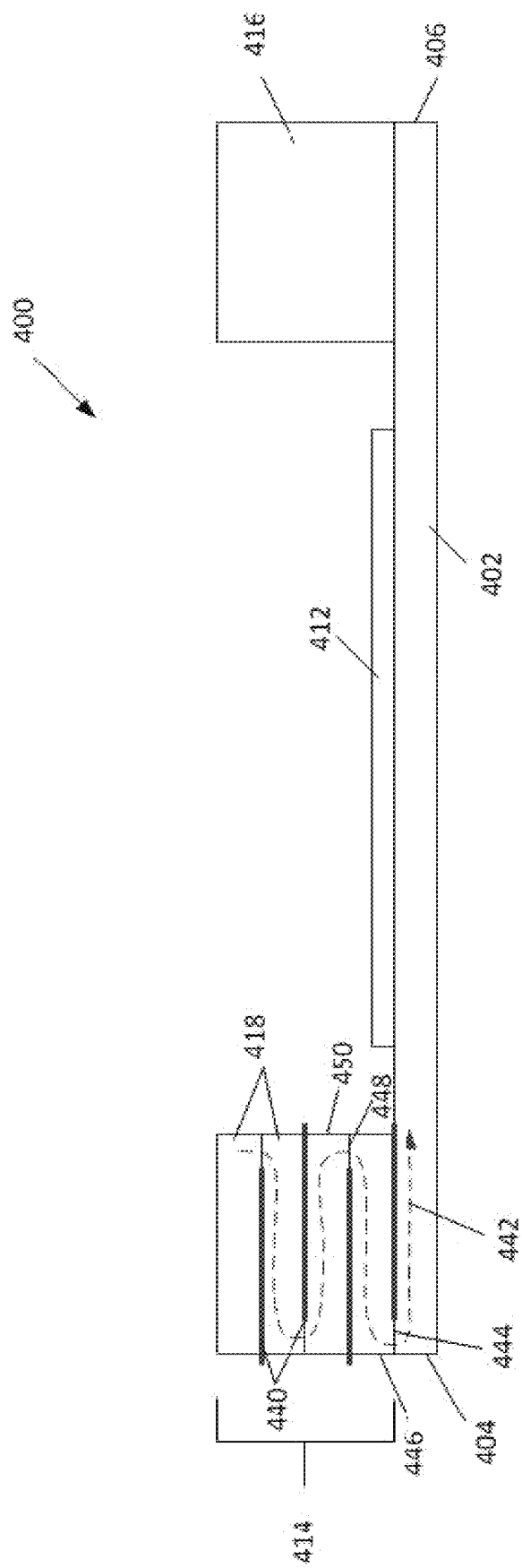

LATERAL FLOW DEVICE AND METHOD OF USE

This application claims the benefit of U.S. Provisional Application 62/366,496 filed on Jul. 25, 2016 which is hereby incorporated by reference in its entirety.

BACKGROUND

Methods for detection of immobilized analytes are commonly employed in the biological sciences. For example, traditional blotting (e.g., Southern, northern, western, far western, eastern, vacuum, middle eastern, eastern-western, and far-eastern blotting, etc.) can be used to detect analytes immobilized on a substrate or membrane or in a matrix (e.g., in agarose or acrylamide). In general, such blotting techniques involve immobilization of the analyte(s) to be detected and contacting the analyte(s) with a binding reagent (e.g., an antibody). Blotting also usually involves multiple washing steps and/or blocking steps between immobilization and final detection. Such washing and blocking steps consume a practitioner's limited time and/or reagents and can be a source of error and irreproducibility.

SUMMARY

Provided herein are lateral flow devices and methods of use.

In an embodiment, the device comprises a wicking pad composed of a porous material, the wicking pad having a region for applying a substrate comprising immobilized analytes (e.g., proteins); and wherein the wicking pad has a first end, a second end and two lateral edges; a first reservoir comprising a stack of a plurality of reagent layers located on the first end of the wicking pad; and a second reservoir comprising an absorbent pad located on the second end of the wicking pad. In some embodiments, each of the plurality of reagent layers comprises a reagent immobilized in an absorbent pad. In some embodiments, each of the reagent layers comprises a thin barrier layer coated or bonded on a portion of a lower surface. In certain embodiments, each of the plurality of reagent layers comprises a reagent in a solution. In some embodiments, each of the plurality of reagent layers comprises a density agent. In some embodiments, the density agent is selected from the group consisting of glycerol, sucrose, trehalose, dextran, and polyethylene glycol. In certain embodiments, each of the plurality of reagent layers has a different reagent therein.

In some embodiments in which each of the plurality of reagent layers comprises a reagent in a solution, the first reservoir is a cylinder or a trough having a fluid flow controller at a first end to control release of the solution from the first reservoir. In certain embodiments, the fluid flow controller is a valve. In some embodiments, the fluid flow controller is a slit having a width ranging from about 0.5 mm to about 2 mm. In some embodiments, the slit has a width of about 0.5 mm or about 1 mm.

In certain embodiments, the reagent in the reagent layer is selected from the group consisting of a primary antibody, a secondary antibody, a first wash solution, and a second wash solution. In some embodiments, the plurality of reagent layers, starting at a reagent layer in contact with the wicking pad, comprises a first reagent layer having a primary antibody, a second reagent layer having a first wash solution, a third reagent layer having a secondary antibody, and a fourth reagent layer having a second wash solution. In some embodiments, the plurality of reagent layers, starting at a reagent layer at or near a first end of the first reservoir, comprises a first reagent layer having a primary antibody, a second reagent layer having a first wash solution, a third reagent layer having a secondary antibody, and a fourth reagent layer having a second wash solution. In certain embodiments, the fourth reagent layer is at least twice the thickness of the third reagent layer. In some embodiments, the first reservoir has a fifth reagent layer comprising the second wash solution. In certain embodiments, the volume of the second wash solution in the first reservoir is at least twice the volume of the secondary antibody.

In embodiment in which each of the plurality of regent layers is formed from an absorbant pad, at least a portion of the first reagent layer is in intimate contact with the wicking pad.

In some embodiments having absorbent reagent layers, the device is sealed in a plastic casing. In some embodiments, the plastic casing comprises a molded bottom portion and a planar coversealed to the bottom portion. In some embodiments, the wicking pad and reservoirs are dry. In some embodiments, at least one of the wicking pad and the first reservoir is wet.

In some embodiments having absorbent reagent layers, the reagent layers are each formed of at least one material selected from the group consisting of cotton, glass fiber, cellulose, a cellulose fiber derivative, sintered glass, sintered polymer, sintered metal, and a synthetic polymer. In certain embodiments, the synthetic polymer is selected from the group consisting of polyacrylamide, nylon, polypropylene, polyethylene, polystyrene, divinylbenzene, polyvinyl, polyvinyl difluoride, high density polyvinyl difluoride, a ($C_2$-$C_6$) monoolefin polymer, a vinylaromatic polymer, a vinylaminoaromatic polymer, a vinylhalide polymer, a ($C_1$-$C_6$) alkyl (meth)acrylate polymer, a(meth)acrylamide polymer, a vinyl pyrrolidone polymer, a vinyl pyridine polymer, a ($C_1$-$C_6$) hydroxyalkyl (meth)acrylate polymer, a (meth)acrylic acid polymer, an acrylamidomethylpropylsulfonic acid polymer, an N-hydroxy-containing ($C_1$-$C_6$) alkyl(meth)acrylamide polymer, and acrylonitrile.

In some embodiments, the substrate is selected from the group consisting of a membrane, glass, plastic, silicon, metal, and metal oxide. In certain embodiments, the membrane is formed of at least one material selected from the group consisting of nitrocellulose, polyvinylidene fluoride, nylon, and polysulfone. In some embodiments, the plastic is selected from the group consisting of polyethylene terephthalate, polypropylene, polystyrene, and polycarbonate.

Also provided are methods of performing a lateral flow assay. In some embodiments in which the first reservoir is comprised of absorbent reagent layers, the method comprises providing the lateral flow device as described above or elsewhere herein; applying running buffer to the wicking pad; applying a substrate comprising proteins (e.g., a western blot) to the region for applying the substrate comprising analytes; optionally wetting the first reservoir with the running buffer; and allowing lateral flow of the running buffer from the first reservoir to the second reservoir such that reagent in the plurality of reagent layers are sequentially transported in the wicking pad and are contacted to the proteins on the substrate. In some embodiments, the allowing lateral flow step comprises allowing the reagents to follow a sinuous path as they flow through the first reservoir and into the wicking pad.

In some embodiments in which the device is sealed in a plastic casing comprising a bottom portion and a cover sealed to the bottom portion, the method further comprises removing the cover and applying running buffer and the substrate to the wicking pad and subsequently placing the cover on the bottom portion to allow for lateral flow from the first reservoir to the second reservoir.

In some embodiments in which the first reservoir is comprised of stacked reagent-containing solutions, the method comprises providing the lateral flow device as described above or elsewhere herein; optionally applying a running buffer to the wicking pad; applying a substrate comprising proteins (e.g., a western blot) to the region for applying the substrate comprising analytes; and allowing lateral flow of the plurality of reagent layers from the first reservoir to the second reservoir such that a plurality of reagents are sequentially transported in the wicking pad and are contacted to the proteins on the substrate.

In some embodiments, the methods further comprise allowing lateral flow of the running buffer or solutions from the first reservoir to the second reservoir such that primary antibodies from a first reagent layer bind to their target proteins, if present on the substrate, followed by allowing a first wash solution from a second reagent layer to remove unbound primary antibodies from the substrate. In some embodiments, the methods further comprise allowing lateral flow of the running buffer or solutions from the first reservoir to the second reservoir such that secondary antibodies or a secondary detection reagent from a third reagent layer are allowed to contact the primary antibodies bound to their target proteins, if present, on the substrate. In some embodiments, the methods further comprise allowing lateral flow of the running buffer or solutions from the first reservoir to the second reservoir such that a second wash solution from a fourth reagent layer is allowed to remove unbound secondary antibodies from the substrate.

In certain embodiments, the method further comprises applying a substantially uniform pressure to the first reservoir. In some embodiments, the method further comprises applying a substantially uniform pressure to both the first and second reservoirs.

In some embodiments, the method further comprises following binding of the primary antibodies to the target proteins, if present, (and optionally contact of the secondary antibodies or secondary detection regents to the primary antibodies), removing the membrane and detecting the binding of the primary antibodies to the target proteins if present.

Also provided is a kit for performing lateral flow. In some embodiments, the kit includes a plurality of absorbant pads for use in forming the first and second reservoirs and a wicking pad, all of which are described herein. In some embodiments, the kit includes reagents (e.g., binding reagents including labeled primary antibody or primary and secondary antibodies, wash solution, and/or running buffer) provided as solutions to be applied to the absorbent reagent layers by the end-user. In some embodiments, the kit contains one or more absorbent reagent layers each with a reagent reversibly bound therein. In certain embodiments, some or all of the reagents are dried onto an absorbent reagent layer. In some embodiments, some or all of the reagents are dried onto an absorbent reagent layer, or portion thereof, in the presence of one or more protein aggregation modifying agents.

In some embodiments, the kit further includes running buffer for performing lateral flow and optionally includes blocking agents (e.g., bovine serum albumin, non-fat dried milk, or casein), surfactants (e.g., Tween 20 or Triton X-100), protein aggregation modifying agents as described herein, macromolecular crowding agents (e.g., dextran, polyethylene glycol and/or Ficoll), and/or agents to promote even flow of reagents and/or promote reaction to molecules on the substrate and minimize background on the substrate. The additional agents can be provided in the kit as a solid or in liquid form. In some embodiments, the kit further includes instructions for carrying out the methods described herein.

BRIEF DESCRIPTION OF THE DRAWINGS

In FIG. 2A, the device is shown in a plastic molded bottom portion of a casing. In FIG. 2B, the device is shown in a casing having a plastic molded bottom portion with an attached cover. FIG. 2B also shows a western blot membrane on a wicking pad of the device.

FIG. 4C depicts a first end of the first reservoir having a fluid flow controller (e.g., a slit) to control release of the solutions from the first reservoir.

FIG. 5 depicts a side view of a lateral flow device according to an embodiment. The lateral flow device includes a first reservoir having a stack of a plurality of reagent layers. Each of the reagent layers has a barrier layer bonded or coated on a portion of a lower surface. The barrier layers control flow of solutions through the reagent layers.

FIGS. 6A-10 show immunoblotting results using the lateral flow device of FIGS. 1-2B.

DETAILED DESCRIPTION

Figure 1:
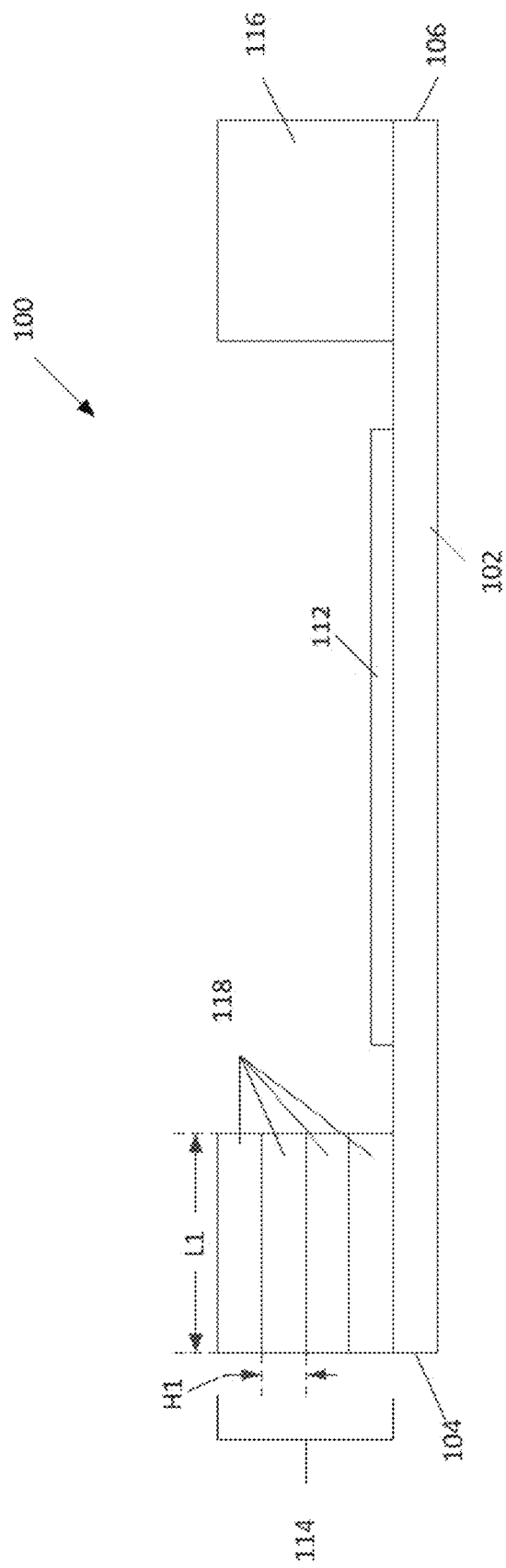
FIG. 1 depicts a side view of a lateral flow device according to an embodiment. The lateral flow device includes a first reservoir having a stack of a plurality of reagent layers. Each reagent layer is an absorbent pad having a reagent immobilized therein.

Described herein are lateral flow devices and methods of using such devices that allow for efficient lateral flow detection of proteins immobilized on substrates (e.g., western blot membranes) using specific binding reagents (e.g., antibodies). Lateral flow devices and methods of using such devices have been discovered that deliver different reagents (e.g., specific binding reagents, running buffer, wash solutions) sequentially and hands-free to a wicking pad in intimate contact with a substrate having proteins thereon. In some embodiments, the devices described herein can be configured in a single-use casing, allowing for an affordable and simple assay format.

I. DEFINITIONS

The term "analyte" refers to a biological molecule, e.g., a protein, nucleic acid, polysaccharide, lipid, antigen, growth factor, hapten, etc., or a portion thereof. Analytes can be irreversibly immobilized on a surface, such as a membrane and detected as described herein.

The term "immobilized" or "embedded" interchangeably refers to reversibly or irreversibly immobilized molecules (e.g., binding reagents or analytes). Reversibly immobilized molecules are immobilized in a manner that allows the molecules, or a portion thereof (e.g., at least 25%, 50%, 60%, 75%, 80% or more of the molecules), to be removed from their immobilized location without substantial denaturation or aggregation. For example, a molecule can be reversibly immobilized in or on an absorbent material (e.g., an absorbent pad) by contacting a solution containing the molecule with the absorbent material, thereby soaking up the solution and reversibly immobilizing the molecule. The reversibly immobilized molecule can then be removed by wicking the solution from the absorbent material, or from one region of the absorbent material to another. In some cases, a molecule can be reversibly immobilized on an absorbent material by contacting a solution containing the molecule with the absorbent material, thereby soaking up the solution, and then drying the solution-containing absorbent material. The reversibly immobilized molecule can then be removed by contacting the absorbent material with another solution of the same or a different composition, thereby solubilizing the reversibly immobilized molecule, and then wicking the solution from the absorbent material, or from one region of the absorbent material to another.

Irreversibly immobilized molecules (e.g., binding reagents or analytes) are immobilized such that they are not removed, or not substantially removed, from their location under mild conditions (e.g., pH between about 4-9, temperature of between about 4-65° C.). Exemplary irreversibly immobilized molecules include protein analytes bound to a nitrocellulose, polyvinylidene fluoride, nylon or polysulfone membrane by standard blotting techniques (e.g., electroblotting). Other exemplary irreversibly immobilized molecules include protein analytes bound to glass or plastic (e.g., a microarray, a microfluidic chip, a glass histology slide or a plastic microtiter plate having wells with bound protein analytes therein).

The term "binding reagent" refers to a reagent that specifically binds to a molecule such as an analyte. While antibodies are described in many contexts herein, it will be understood that other binding agents can be used instead of antibodies as preferred by the user. A wide variety of binding reagents are known in the art, including antibodies, aptamers, affimers, lipocalins (e.g., anticalins), thioredoxin A, bilin binding protein, or proteins containing an ankyrin repeat, the Z domain of staphylococcal protein A, or a fibronectin type III domain.

The term "specifically bind" refers to a molecule (e.g., binding reagent such as an antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, 100-fold, or 1000-fold or more greater affinity.

The term "antibody" refers to a polypeptide comprising a framework region from an immunoglobulin gene, or fragments thereof, that specifically bind and recognize an antigen, e.g., a particular analyte. Typically, the "variable region" contains the antigen-binding region of the antibody (or its functional equivalent) and is most critical in specificity and affinity of binding. See Paul, *Fundamental Immunology* (2003). Antibodies include for example chimeric, human, humanized antibodies, or single-chain antibodies.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

As used in this specification and the appended claims, the singular forms "a", "an", and "the" include plural referents unless the content clearly dictates otherwise. As used herein, the term "about" refers to the recited number and any value within 10% of the recited number. Thus, "about 5" refers to any value between 4.5 and 5.5, including 4.5 and 5.5.

II. DEVICES

Figure 2A:
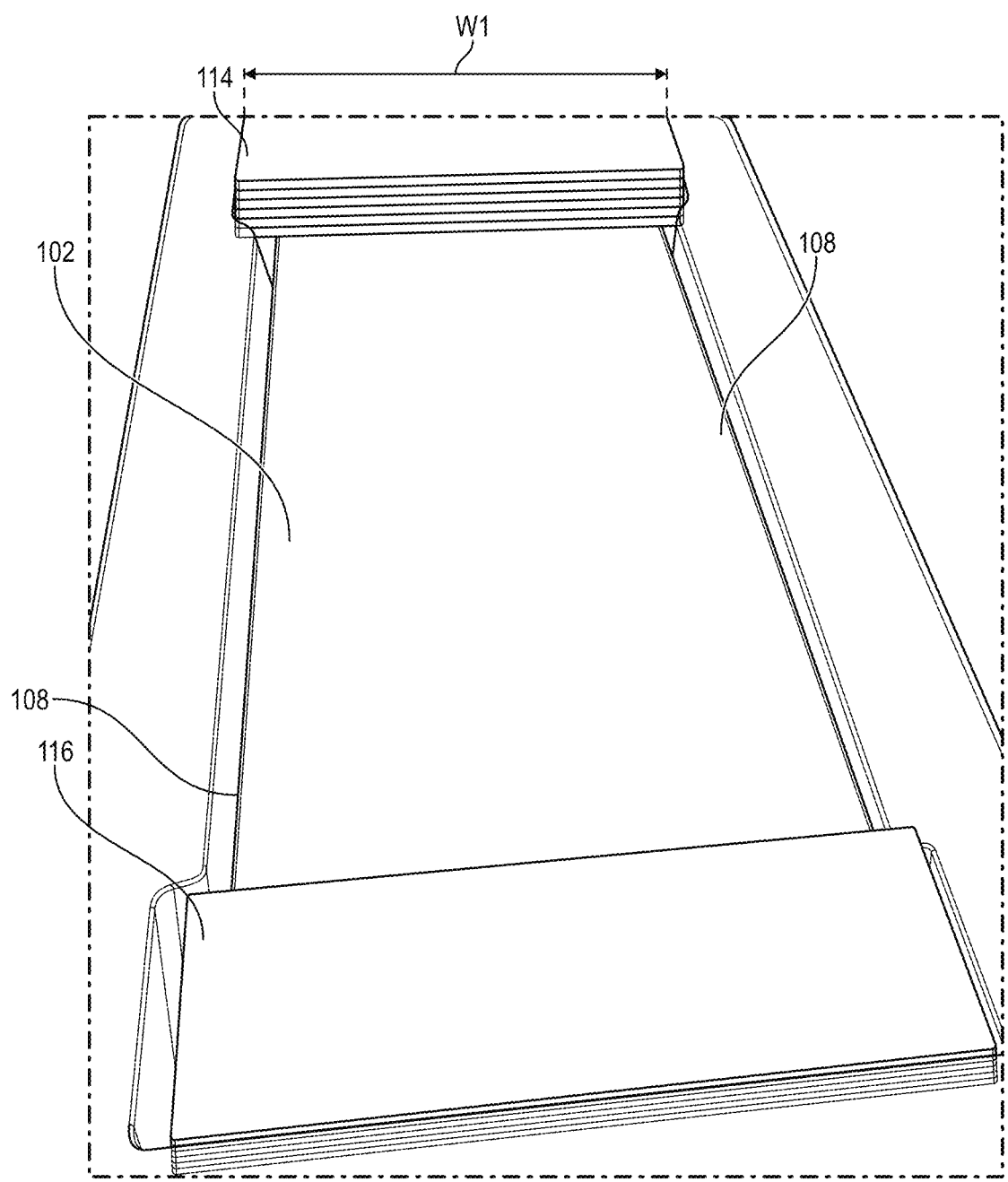
FIGS. 2A and 2B depict a lateral flow device according to an embodiment.
Figure 2B:
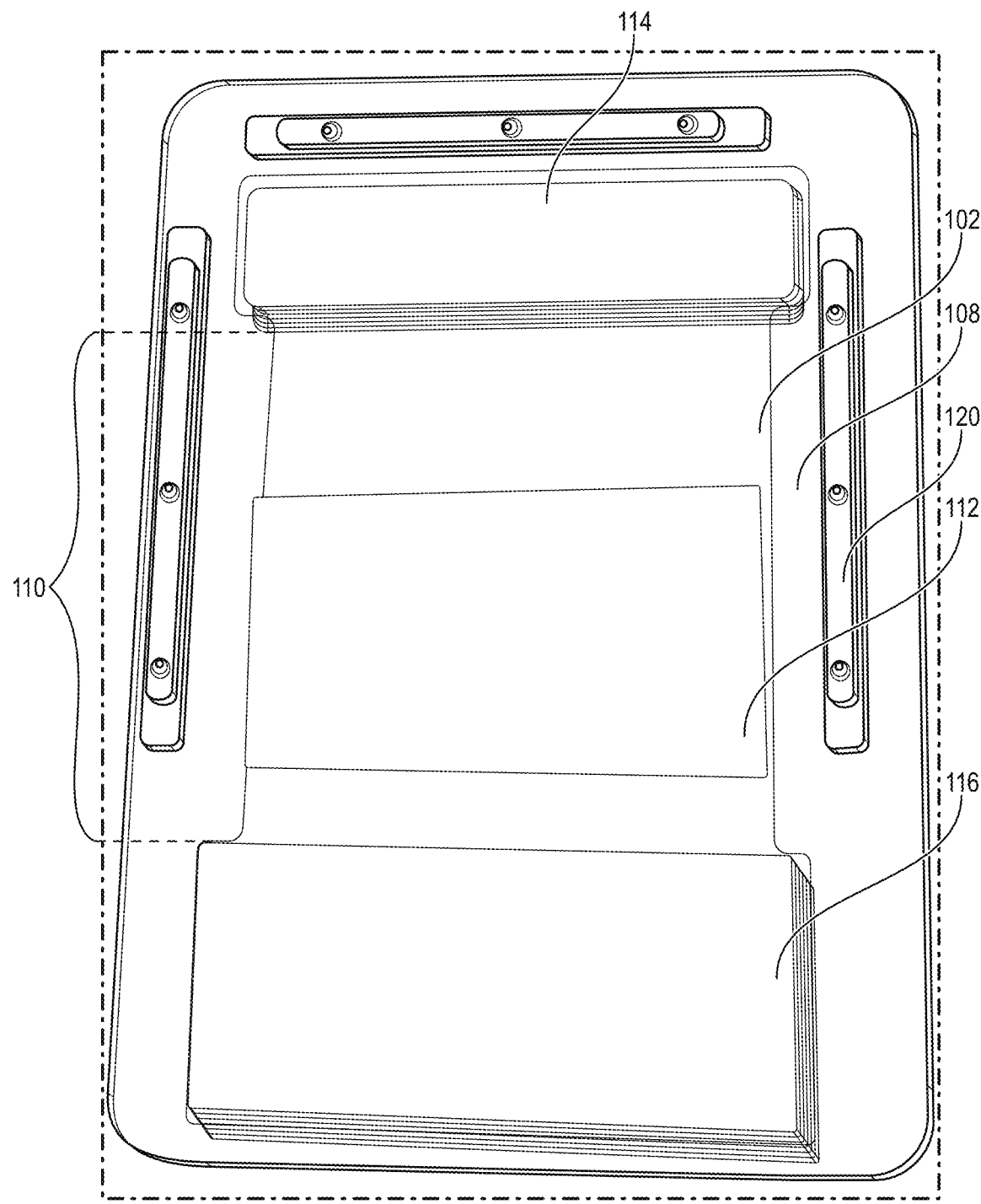

FIGS. 1, 2A and 2B illustrate an embodiment of a lateral flow device 100 for detecting proteins on a substrate. The lateral flow device 100 includes a wicking pad 102 having a first end 104, a second end 106, two lateral edges 108, and a region 110 for applying a substrate 112 (e.g., a membrane) comprising immobilized analytes (e.g., proteins) to be detected. The lateral flow device 100 also includes a first reservoir 114 located on or at the first end 104 of the wicking pad 102. The first reservoir 114 supplies liquid (e.g., buffers and detection reagents) to the wicking pad 102. In some embodiments, the first reservoir 114 is in intimate contact with the wicking pad 102. The lateral flow device 100 further includes a second reservoir 116 located on or near the second end 106 of and in intimate contact with the wicking pad 102. The second reservoir 116 acts as a pump by wicking the liquid from the first reservoir 114 to the dry second reservoir 116.

The wicking pad 102 is a flat absorbent material onto which is placed the substrate 112 comprising immobilized analytes (e.g., a western blot). The wicking pad 102 may include drawings/markings or other indications for where a user should place the substrate 112. Alternately, the drawing/markings may be on the device casing. In some embodiments, the substrate 112 is placed on the wicking pad 102 downstream from the first reservoir 114 and upstream from the second reservoir 116 (e.g., between the first reservoir 114 and the second reservoir 116).

The wicking pad 102 has a width, a length, and a height (e.g., a thickness). The wicking pad 102 can be any size and shape. In certain embodiments, the wicking pad 102 is planar, e.g., the wicking pad 102 can approximate or be a rectangular plane. In some cases, the length and the width of the wicking pad 102 are at least about 2-fold, 5-fold, 10-fold, 100-fold or more larger than the height (i.e., thickness). In some embodiments, the wicking pad 102 has an impermeable, or substantially impermeable backing.

Exemplary sizes for wicking pads include, without limitation, wicking pads that are at least about 0.25 cm, 0.5 cm, 1 cm, 2 cm, 3 cm, 4 cm, 5 cm, 6 cm, 7 cm, 8 cm, 10 cm, 12 cm, 15 cm, 20 cm, 30 cm or more in at least one dimension. Exemplary sizes of rectangular planar wicking pads include wicking pads that are about 1 cm×1 cm, 7×8.5 cm, 8.5×13.5 cm, 10 cm×15 cm, or 25×28 cm in length and width respectively. Exemplary sizes further include 8.5 cm×9 cm, 7 cm×9 cm, 8 cm×10.7 cm, 10 cm×10 cm, 7 cm×8.5 cm, 8.3 cm×7.3 cm, 8 cm×8 cm, 8.3 cm×13 cm, 10.8 cm×13.5 cm. In some embodiments, the wicking pad 102 is 18 cm in length by 10 cm in width. In some cases, the wicking pad 102 is 18±0.5, 1, 2, or 3 cm in length by 10±0.5, 1, 2, or 3 cm in width.

In some embodiments, the wicking pad 102 is configured to have a high solution capacity and a lateral flow rate. In some cases, the high solution capacity and lateral flow rate are provided by having a wicking pad 102 with substantial height (e.g., thickness). In some cases, the wicking pad 102 is about 10, 9, 8, 7, 6, 5, 4, 3, 2, 1, 0.75, 0.5, or about 0.2 mm thick. In some cases, the wicking pad 102 is between about 0.05 mm and about 0.5 mm thick.

The first reservoir 114 includes a stack of a plurality of reagent layers 118, each having a reagent (e.g., primary antibodies, secondary antibodies, running buffer, and/or wash buffer) immobilized or embedded therein. In some embodiments, each of the plurality of reagent layers has a different reagent immobilized or embedded therein. The first reservoir 114 is in liquid communication with the wicking pad 102 (i.e., liquid, when present in the first reservoir 114, can flow from the first reservoir 114 to the wicking pad 102) and is configured to sequentially deliver reagents from the plurality of reagent layers 118 to the wicking pad 102. The embedded reagents will generally be embedded and dried into the absorbent pad of the reagent layer such that they are immobile until contacted by an aqueous fluid front under lateral flow and released at a user-defined event.

Each of the reagent layers 118 has a width W1, a length L1, and a height H1 (e.g., a thickness). In certain embodiments, each reagent layer is planar, e.g., each reagent layer can approximate or be a rectangular plane. In some cases, the length L1 and the width W1 of each reagent layer are at least about 2-fold, 5-fold, 10-fold, 100-fold or more larger than the height (i.e., thickness).

In the embodiment shown in FIGS. 1, 2A and 2B, each of the plurality of reagent layers 118 is an absorbent pad and a reagent is immobilized in the absorbent pad. In certain embodiments, each of the plurality of reagent layers 218 is a solution having a reagent therein. In some embodiments, each of the solutions has a different reagent therein. In embodiments in which the reagent layers 218 are solutions, a first reservoir 214 is a cylinder (see FIG. 3) or a trough having a fluid flow controller 222 (e.g., a valve) at a first end 220 to control release of the solutions from the first reservoir 214. In some embodiments, the first reservoir also has a fluid flow controller (e.g., a valve) at a second end 224.

In some embodiments, a first reservoir 314 is a rectangular-shaped trough (see FIGS. 4A-4C) having a plurality of reagent layers 318, each of which is a solution having a reagent therein. The first reservoir 314 includes a first end 320 and a second end 324. The first end 320 has a fluid flow controller 322 (e.g., a slit) to control release of the solutions from the first reservoir 314. In embodiments in which the fluid flow controller 322 is a slit, the slit can have a width W2 (e.g., a short dimension) ranging from about 0.5 mm to about 2 mm and a length L2 (e.g., a long dimension) ranging from about 8.5 cm to about 20 cm. In some embodiments, the width W2 is 0.5 mm, 1 mm, or 2 mm. In certain embodiments, the length L2 is 8.5 cm, 9.5 cm, 13.5 cm or 20 cm. The dimensions of the slit and the viscosity of the reagent solutions can affect the rate at which the solutions exit the slit and can be adjusted according to user preference. For example, as the width W2 decreases, the rate at which the solutions exit the slit also decreases, which increases the overall lateral flow process time for the device 100.

The fluid flow controller 322 and/or an opening 326 on the second end 324 can be sealed or covered with a removable metal foil or plastic foil (e.g., tape).

Referring again to FIGS. 1-2B, in some embodiments, each reagent layer is sized to match the width of the wicking pad 102 and has a width that is at least about 3-fold, 4-fold, 5-fold, 6-fold, 8-fold, 10-fold, 13-fold, 17-fold, 20-fold, 27-fold or more larger than the length.

Exemplary sizes for each reagent layer include, but are not limited to, at least about 0.25 cm, 0.5 cm, 1 cm, 2 cm, 2.5 cm, 3 cm, 3.5 cm, 4 cm, 5 cm, 6 cm, 7 cm, 8 cm, 8.5 cm, 9.5 cm, 10 cm, 13.5 cm, 20 cm or more in at least one dimension. Exemplary sizes of each rectangular planar reagent layer include, but are not limited to, about 0.5 cm×8.5 cm, 1 cm×1 cm, 2.5 cm×about 8.5 cm, 2×13.5 cm, 3×13.5 cm, or 3.5 cm×20 cm in length L1 and width W1 respectively. As used herein, the "length L1" is based on the direction of flow and is the shortest dimension. In some embodiments, each reagent layer is 3 cm in length L1 by 10 cm in width W1. In some cases, each reagent layer is 1±0.5, 1, or 2 cm in length L1 by 10±0.5 cm or 14±0.5 cm in width W1.

In some embodiments, each of the reagent layers 118 are formed of an absorbent, porous material and is configured to have a high solution capacity. In some cases, the high solution capacity is provided by having a reagent layer with substantial height (e.g., thickness).

In some cases, the reagent layer is about 10, 9, 8, 7, 6, 5, 4, 3, 2, 1, 0.75, 0.5, or about 0.2 mm thick. In some cases, the reagent layer is between about 0.05 mm and about 0.5 mm thick.

Each of the reagent layers 118 generally has a large surface area due to the presence of a plurality of pores. The large surface area can increase the loading capacity of the reagent layer for one or more reagents or one or more solutions containing a reagent. In some embodiments, the reagent layers 118 have a specific surface area of at least about 0.001 $m^2/g$, 0.02 $m^2/g$, 0.1 $m^2/g$, 0.5 $m^2/g$, 1 $m^2/g$ 10 $m^2/g$, or more as measured by standard techniques.

In some embodiments, each reagent layer and/or the wicking pad 102 can have a particular pore size, a particular average pore size, or a particular pore size range. For example, each reagent layer and/or the wicking pad 102 can contain 0.1 μm pores, 0.2 μm pores, 0.45 μm pores, or 1, 2, 4, 5, 6, 7, 8, 10, 15, 20 μm pores, or pores larger than about 20 μm. As another example, the each reagent layer and/or the wicking pad 102 can contain pores that average 0.1, 0.2, 0.45, 1, 2, 4, 5, 6, 7, 8, 10, 15, or 20 μm, or more in size. As another example, each reagent layer and/or the wicking pad 102 can contain pores that range about 0.1-8 µm, 0.2-8 µm, 0.45-8 µm, 1-8 µm, 0.1-4 µm, 0.1-2 µm, 0.1-1 µm, 0.1-0.45 µm, 0.2-8 µm, 0.2-4 µm, 0.2-2 µm, 0.2-1 µm, 0.2-0.45 µm, 0.45-8 µm, 0.45-4 µm, 0.45-2 µm, 0.45-1 µm in size. In some cases, each reagent layer and/or the wicking pad 102 can contain pores that are less than about 20 µm in size. For example, each reagent layer and/or the wicking pad 102 can be composed of a material in which at least about 50%, 60%, 70%, 80%, 90% or more of the pores are less than about 20, 15, 10, or 5µm in size. In some cases, the pores in a reagent layer are large enough to contain one or more proteins of average size (e.g., about 1 nm). For example, the pores can be at least 1 nm in size, at least 5 nm in size, at least 10, 100, or 500 nm in size. Alternatively, at least 50%, 60%, 70%, 80%, 90% or more of the pores can be more than 1, 5, 10, 50, 100, or 500 nm in size. As used herein, pore size can be measured as a radius or a diameter. In some cases, each reagent layer and/or the wicking pad 102 contains porous polyethylene, such as porous polyethylene having a pore size between 0.2 and 20 microns, or between 1 and 12 microns. Each reagent layer and/or the wicking pad 102 can have a different pore size in different regions of the pad or layer. For example, the wicking pad 102 can have a lateral flow region that has a different pore size or pore size range.

Each reagent layer and/or the wicking pad 102 can be treated or functionalized to minimize non-specific reagent binding, increase lateral flow, increase wicking, or to reduce protein aggregation. For example, each reagent layer and/or the wicking pad 102, or a portion thereof, can be treated to alter the hydrophilicity or alter the hydrophobicity of the treated area. In some cases, altering the hydrophilicity or hydrophobicity of a reagent layer can increase binding reagent loading, decrease binding reagent aggregation or denaturation, create mask regions in which binding reagent is excluded from or not loaded, or direct flow of binding reagents when the reagent layer is wet. In some cases, the reagent layer contains a protein aggregation modifying agent as described herein.

Referring to FIG. 5, in some embodiments, each reagent layer 418 has a barrier layer 440 coated or bonded on a portion of a lower surface to control flow of reagent solutions through a first reservoir 414 of a lateral flow device 400. In some embodiments, the barrier layers 440 are positioned such that solutions flowing sequentially from the reagent layers 418 follow a sinuous path 442 to the wicking pad 402. For example, alternate reagent layers can have a barrier layer on substantially all but a first region 444 of the lower surface near a first edge 446. The other alternating reagent layers can have a barrier layer 440 on substantially all but a second region 448 on a lower surface near a second edge 450. In certain embodiments, the barrier layer 440 spans the width of the lower surface of each reagent layer. In some embodiments, the first and/or second regions 444, 448 of the reagent layers that do not contain a barrier layer span the width of the reagent layer 418. In some embodiments, the barrier layer 440 can extend past the first edge 446 or the second edge 450 of the reagent layer so that solutions will flow through the regions having no barrier layer and not down the edge of the reagent layer having a barrier layer extending therefrom. The thin barrier layer 440 can be formed from materials including, but not limited to, plastic foil, metal foil, glass, and/or wax. Plastics from which the barrier layer 440 can be formed include, but are not limited to, polyvinylidine chloride, low-density polyethylene, polyethylene terephthalate, polypropylene, polystyrene, and/or polycarbonate. Processes by which the barrier layer 440 can be bonded to the reagent layer 418 can include bonding with adhesive, thermal bonding, or organic solvent bonding with or without pressure.

Each reagent layer can be marked or annotated such that the origin, composition, or location of a reversibly immobilized binding reagent (e.g., a primary antibody) is recorded. For example, one or more regions containing reversibly immobilized binding reagent(s) can be visually discernible, such that one of skill in the art can determine the location of the reversibly immobilized binding reagent. In some cases, the name of the binding reagent (e.g., anti-phospho PIK3), identity (e.g., catalog number), amount, lot number, etc. can be printed, stamped, or otherwise indicated on a portion of the reagent layer. In some cases, each reagent layer is marked or annotated such that the proper orientation for use in the lateral flow blotting device 100 is discernible.

Figure 3:
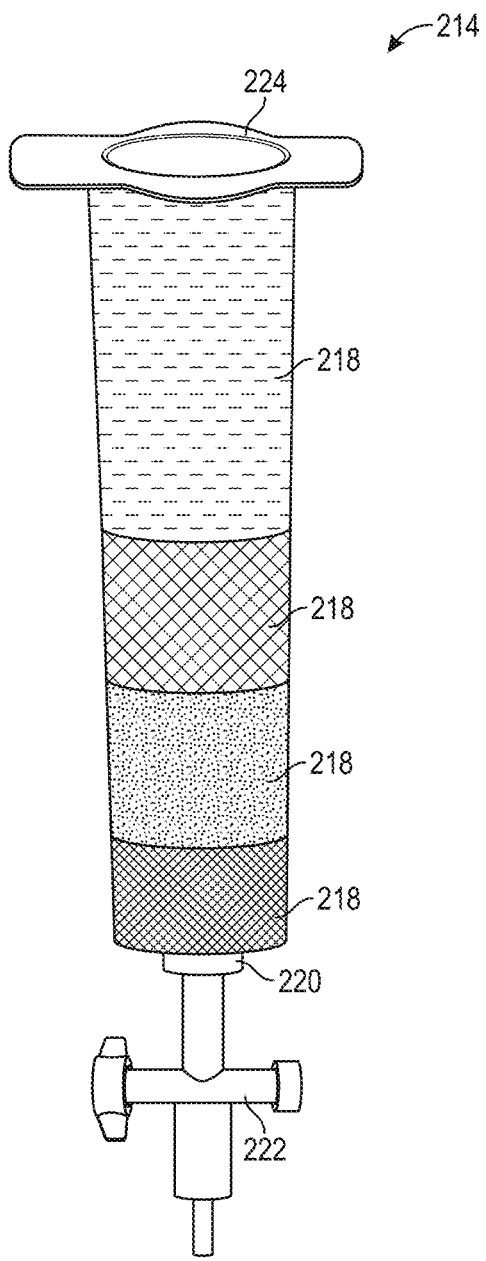
FIG. 3 depicts a first reservoir of a lateral flow device according to an embodiment in which each reagent layer is a solution contained in the first reservoir (e.g. a cylinder). The first end of the first reservoir has a fluid flow controller (e.g., a valve) to control release of the solutions from the first reservoir.
Figure 4A:
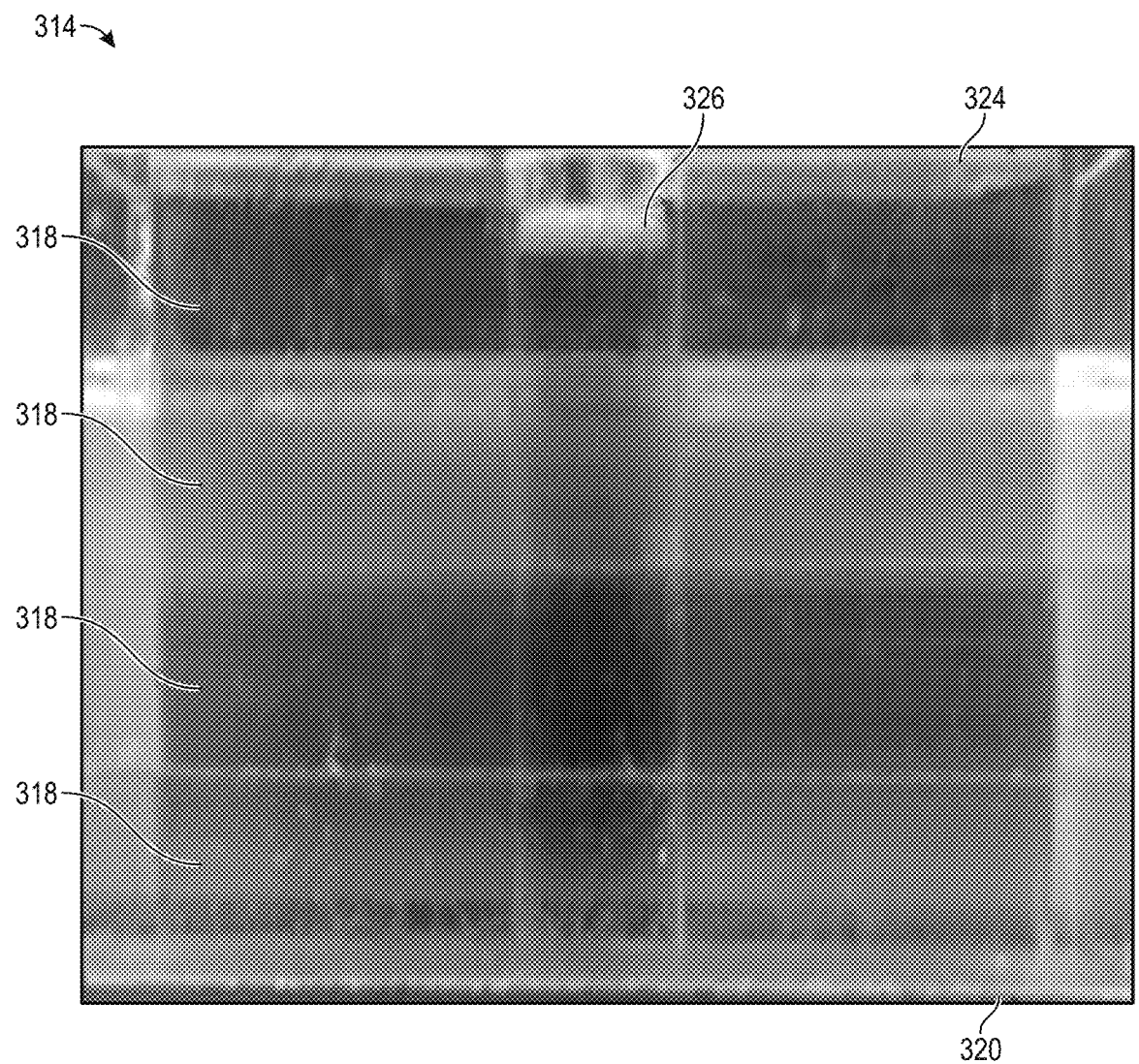
FIGS. 4A, 4B and 4C depict side, top and bottom views, respectively, of a first reservoir of a lateral flow device according to an embodiment in which each reagent layer is a solution contained in the first reservoir (e.g. a trough).

In some embodiments, the plurality of reagent layers 118, 218, 318 includes a first reagent layer comprising primary antibody (e.g., labeled primary antibody) and a second reagent layer comprising a first wash solution. In some embodiments, the reagent layers 118, 218, 318 are different and include a first reagent layer comprising primary antibody, a second reagent layer comprising a first wash solution, a third reagent layer comprising secondary antibody or a secondary detection reagent, and a fourth reagent layer comprising a second wash solution (FIGS. 1-4A). As depicted in FIGS. 1-2B, the first layer is in intimate contact with the wicking pad 102. As depicted in FIGS. 3 and 4A, the first layer is the layer at or near the first end 220, 320 of the first reservoir 214, 314. In some embodiments, the plurality of reagent layers 118, 218, 318 has two or more layers of the same reagent. In such embodiments having two layers of the same reagent, the first reservoir 114, 214, 314 will include twice the volume of the reagent. For example, in some embodiments, the reagent layers 118, 218, 318 further include a fifth reagent layer comprising the second wash solution such that the first reservoir 114, 214, 314 includes two layers or twice the volume of the second wash solution. In embodiments in which the reagent layers 118 are formed of absorbent material, one or more reagent layers 118 can be at least twice the thickness of the other layers. For example, the fourth reagent layer having the second wash solution can be at least twice the thickness of the third reagent layer having secondary antibody.

Each of the reagent layers 118, 218, 318 can further include a density agent. Having a density agent in each of the reagent layers 118, 218, 318 of the first reservoir 114, 214, 314 can maintain reagents in discrete zones to minimize mixing and to allow for timed, sequential delivery of reagents to the wicking pad 102. Examples of density agents include, but are not limited to, glycerol, sucrose, trehalose, dextran, and polyethylene glycol.

Each of the reagent layers 118, 218, 318 can further include one or more dyes or indicators for monitoring the lateral flow (e.g., the progress) of the reagent out of the first reservoir 114 and into/through the wicking pad 102.

The second reservoir 116 acts as a wicking "pump" for the lateral flow system and includes one or more absorbent pads. In some embodiments, the second reservoir 116 can be the wicking pad 102. The second reservoir 116 is in liquid communication with the wicking pad 102 (i.e., liquid, when present in the wicking pad 102 can flow from the wicking pad 102 to the second reservoir 116).

The reagent layers 118, the wicking pad 102, and the second reservoir 116 are generally formed of a bibulous material and can be made out of, for example, natural fibers, synthetic fibers, glass fibers or blends thereof. Non-limiting examples include cotton, glass, and combinations thereof. There are many commercial materials available for diagnostic uses from vendors such as Ahlstrom, GE, PALL, Millipore, Sartorius, S&S etc.

The bibulous material can include, but is not limited to, polymer containing material. The polymer can be in the form of polymer beads, a polymer membrane, or a polymer monolith. In some cases, the polymer is cellulose. Cellulose containing pads include paper, cloth, woven, or non-woven cellulose substrates. Cloth pads include those containing a natural cellulose fiber such as cotton or wool. Paper pads include those containing natural cellulose fiber (e.g., cellulose or regenerated cellulose) and those containing cellulose fiber derivatives including, but not limited to cellulose esters (e.g., nitrocellulose, cellulose acetate, cellulose triacetate, cellulose proprionate, cellulose acetate propionate, cellulose acetate butyrate, and cellulose sulfate) and cellulose ethers (e.g., methylcellulose, ethylcellulose, ethyl methyl cellulose, hydroxyethyl cellulose, hydroxyethyl methyl cellulose, hydroxypropyl methyl cellulose, ethyl hydroxyethyl cellulose, and carboxymethyl cellulose). In some cases, the cellulose pads contains rayon. In some cases, the pad is paper, such as a variety of WHATMAN® paper.

The bibulous material can also include, but is not limited to, a sintered material. For example, the bibulous material can contain a sintered glass, a sintered polymer, or sintered metal, or a combination thereof. In some cases, the sintered material is formed by sintering one or more of powdered glass, powdered polymer, or powdered metal. In other cases, the sintered material is formed by sintering one or more of glass, metal, or polymer fibers. In still other cases, the sintered material is formed from the sintering of one or more of glass, polymer, or metal beads.

The bibulous material can also contain, but is not limited to, one or more non-cellulosic polymers, e.g. a synthetic polymer, a natural polymer, or a semisynthetic polymer. For example, the material can contain a polyester, such as polyglycolide, polylactic acid, polycaprolactone, polyethylene adipate, polyhydroxylalkanoate, polyhydroxybutyrate, poly(3-hydroxybutyrate-co-3-hydroxyvalerate, polyethylene terephthalate, polybutylene terephthalate, polytrimethylene terephthalate, polyethylene naphthalate, Vectran®. In some cases, the polymer is spunbound, such as a spunbound polyester.

Additional synthetic polymers include, but are not limited to nylon, polypropylene, polyethylene, polystyrene, divinylbenzene, polyvinyl, polyvinyl difluoride, high density polyvinyl difluoride, polyacrylamide, a $(C_2-C_6)$ monoolefin polymer, a vinylaromatic polymer, a vinylaminoaromatic polymer, a vinylhalide polymer, a $(C_1-C_6)$ alkyl (meth)acrylate polymer, a(meth)acrylamide polymer, a vinyl pyrrolidone polymer, a vinyl pyridine polymer, a $(C_1-C_6)$ hydroxyalkyl (meth)acrylate polymer, a (meth)acrylic acid polymer, an acrylamidomethylpropylsulfonic acid polymer, an N-hydroxy-containing $(C_1-C_6)$ alkyl(meth)acrylamide polymer, acrylonitrile or a mixture of any of the foregoing.

In some embodiments, the reagent layers 118 are formed from non-bibulous material in which liquids flow by capillary action. Such material includes, but is not limited to, high density or ultra high molecular weight polyethylene sheet material manufactured by Porex Technologies Corp.

In some embodiments, the wicking pad 102 can be backed to prevent flow on the underside. This can be achieved, for example, by using an adhesive backing to which the wicking pad 102 is adhered. The nature of the adhesive may affect the assay performance (i.e., flow characteristics, reagent stability etc.) such that the adhesive can be optimized for the desired assay. In some embodiments, the adhesive may be part of the molded bottom portion of the device 100.

The substrate 112 is generally planar in shape and can be, for example, a membrane formed of nitrocellulose, polyvinylidene fluoride, nylon, or polysulfone. Other materials from which the substrate 112 can be formed include, but are not limited to, glass, plastic, silicon, metal, and/or metal oxide that is bare or is functionalized with polymers. Plastic materials from which the substrate 112 can be formed include, but are not limited to, polyethylene terephthalate, polypropylene, polystyrene, and/or polycarbonate. Examples of polymers with which to functionalize the surface of substrates formed from metal or metal oxide include glycidoxypropyltriethoxysilane, poly-L-lysine, polybrene, polyethylene glycol polymers, dextran polymer, aminopropylsilane, caroxysilane, hydrogels and polymer brushes, and/or self-assembled monolayers of e.g. functionalized alkyl thiols, dendrimers or oligonucleotides.

The bibulous components can be contained and sealed in a waterproof casing 120. In some embodiments, the casing 120 will be plastic or other inexpensive waterproof material. The casing 120 can, for example, be vacuum or injection molded or otherwise constructed. In some embodiments, the casing 120 comprises a molded bottom portion and a generally planar cover or plate fitted (e.g., snap fit) to the bottom portion. An example of such a casing 120 is displayed in FIG. 1B. In this embodiment, the wicking pad and the first and second reservoirs 114, 116 are contained in a well or section in a molded bottom portion. In some embodiments the casing 120 (e.g, the bottom portion and/or the cover) does not contact the wicking pad 102. In certain embodiments, the bottom portion is planar and the first and second reservoirs 114, 116 are enclosed by a molded cover. In some embodiments, the cover is molded such that the cover contacts and exerts an even and downward force on the first reservoir 114 when the cover is attached to the bottom portion. Exerting an even and downward force on the entire first reservoir 114 results in uniform contact between the reagent layers 118. In certain embodiments, the cover is provided in more than one segment. For example, the cover can include a first segment and a second segment. The first segment can be removable and can cover the first reservoir 114 and the substrate region 110 of the device 100. The second segment can cover the second reservoir 116 and can be removable or welded to the bottom portion.

A. Exemplary Detection Reagents i. Binding Reagents

Binding reagents are described herein for detection of analytes. In some cases, the binding reagents are antibodies (e.g., primary or secondary antibodies). Primary antibodies can be used to bind to an analyte. In some cases, the primary antibody is labeled enabling detection of the primary antibody and consequently detection of the analyte. In some cases, the primary antibody is detected by binding to a labeled secondary binding reagent, such as a labeled secondary antibody. In some cases, tertiary binding reagents are utilized to detect complexes containing the analyte and the primary and secondary binding reagent.

Binding reagents can be provided on or in one or more reagent layers 118, 218 in the first reservoir 114, 214 or can be supplied separately. In some cases, a reagent layer 118 contains one or more binding reagents dried thereon. The dried binding reagent(s) can be reconstituted by contacting the reagent layer 118 with an aqueous solution. In some cases, the aqueous reconstitution buffer can contain one or more re-wetting reagents including salts, buffers, or a protein aggregation modifying agent as described herein. Alternatively, the binding reagent can be present in a solution and the binding agent is reversibly immobilized in the reagent layer 118 by dipping the reagent layer in the solution. In some cases, the binding reagent(s) are stored in the reagent layer 118, 218 (e.g., in the first reservoir 114, 214). For example, binding reagent(s) can be stored dry, substantially dry, or in solution in the reagent layers for at least about a day, three days, 7-10 days, at least about a month, two months, 3 months, six months, a year or longer. In some cases, the binding reagents and reagent layers are suitable for storage (e.g., at about 4, 5, 6, 7, 8, 10, 12, 14, 16, 18, 20, 22, 25, 30, 35, or 37° C. or more) for at least about a day, three days, 7-10 days, at least about a month, two months, 3 months, six months, a year or longer.

ii. Labels

Analytes can be detected by detecting a label that is linked to a binding reagent. The label can be linked directly to the binding reagent (e.g., by a covalent or other bond to the primary antibody) or the attachment can be indirect (e.g., using a chelator or linker molecule). The terms "label" and "detectable label" are used synonymously herein. In some embodiments, each label (e.g., a first label linked to a first binding reagent, a second label linked to a second binding reagent, etc.) generates a detectable signal and the signals (e.g., a first signal generated by the first label, a second signal generated by the second label, etc.) are distinguishable. In some embodiments, the two or more binding reagent labels comprise the same type of agent (e.g., a first label that is a first fluorescent agent and a second label that is a second fluorescent agent). In some embodiments, the two or more binding reagent labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, colloidal gold, and combinations thereof. In some embodiments, the label can include an optical agent such as a chromophore, fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Chromophores include co-enzymes or co-factors that have a detectable absorbance. In some cases, a binding reagent can be detected by detecting the intrinsic absorbance of a peptide bond at, e.g., 220 or 280 nm.

Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. In some embodiments, 2, 3, 4, 5, or more binding reagents are each labeled with an optical agent such as a fluorescent agent (e.g., a first binding reagent labeled with a first fluorescent label, a second binding reagent labeled with a second fluorescent label, etc.), and each binding reagent that is labeled with an optical agent is detected by detecting a signal generated by the optical agent (e.g., a fluorescent signal generated by a fluorescent label). In some embodiments, all of the binding reagents are labeled with an optical agent, and each optical agent-labeled binding reagent is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, 2, 3, 4, 5, or more binding reagents are each labeled with a radioisotope (e.g., a first binding reagent labeled with a first radioisotope, a second binding reagent labeled with a second radioisotope, etc.), and each binding reagent that is labeled with a radioisotope is detected by detecting radioactivity generated by the radioisotope. For example, one binding reagent can be labeled with a gamma emitter and one binding reagent can be labeled with a beta emitter. Alternatively, the binding reagents can be labeled with radionuclides that emit the same particle (e.g., alpha, beta, or gamma) at different energies, where the different energies are distinguishable. In some embodiments, all of the binding reagents are labeled with a radioisotope and each labeled binding reagent can be detected by detecting radioactivity generated by the radioisotope.

In some embodiments, the label is an enzyme, and the binding reagent is detected by detecting a product generated by the enzyme. Examples of suitable enzymes include, but are not limited to, urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm, or a chemiluminescent substrate (e.g., Clarity from Bio-Rad Laboratories), which yields detectable light. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some embodiments, 2, 3, 4, 5, or more binding reagents are each labeled with an enzyme (e.g., a first binding reagent labeled with a first enzyme, a second binding reagent labeled with a second enzyme, etc.), and each binding reagent that is labeled with an enzyme is detected by detecting a product generated by the enzyme. In some embodiments, all of the binding reagents are labeled with an enzyme, and each enzyme-labeled binding reagent is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag, eXact-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length.

In some embodiments, the label is a nucleic acid barcode. As used herein a "barcode" is a short nucleotide sequence (e.g., at least about 4, 6, 8, 10, or 12, nucleotides long) that uniquely defines a labeled molecule, or a second molecule bound to the labeled binding reagent.

The length of the barcode sequence determines how many unique samples can be differentiated. For example, a 4 nucleotide barcode can differentiate $4^4$ or 256 samples or less, a 6 nucleotide barcode can differentiate 4096 different samples or less, and an 8 nucleotide barcode can index 65,536 different samples or less. The use of barcode technology is well known in the art, see for example Katsuyuki Shiroguchi, et al., "Digital RNA sequencing minimizes sequence-dependent bias and amplification noise with optimized single-molecule barcodes", PNAS 2012 Jan. 24; 109(4):1347-52; and Smith, A M et al., "Highly-multiplexed barcode sequencing: an efficient method for parallel analysis of pooled samples", Nucleic Acids Research 2010 July; 38(13):e142

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to binding reagents such as proteins (e.g., antibodies) are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase assay. See, e.g., Maeda et al., *J. Biolumin Chemilumin* 1989, 4:140-148.

B. Protein Aggregation Modifying Agents

Described herein are protein aggregation modifying agents. Protein aggregation modifying agents can be utilized to reduce or eliminate aggregation or denaturation of binding reagents, such as proteins (e.g., antibodies), stored on, or delivered from, a reagent layer. For example, protein aggregation modifying agents can be utilized to reduce or eliminate aggregation or denaturation of primary antibodies stored in, or delivered from, the reagent layers 118, 218. In some cases, protein aggregation modifying agents can be utilized to facilitate lateral flow of binding reagents in the lateral flow region 110 of the wicking pad 102.

In some cases, protein aggregation modifying agents that act to displace proteins from the air-water interface and thereby protect them from denaturation and aggregation are particularly effective in reducing the aggregation of binding reagents immobilized on a reagent layer. In other cases, the protein aggregation modifying agent directly affects the stability of the binding reagent by binding to the binding reagent and/or stabilizing the binding reagent. In other cases, the protein aggregation modifying agent acts to shift the equilibrium away from a denatured or unfolded state and thus reduce aggregation. For example, in some cases, the interaction between the protein aggregation modifying agent and the binding reagent is thermodynamically disfavored due to strong repulsion between an amide backbone of the binding reagent and the protein aggregation modifying agent. Thus, unfolding of the binding reagent in the presence of the protein aggregation modifying agent is disfavored because unfolding exposes more amide backbone surface to the protein aggregation modifying agent.

Protein aggregation modifying agents can be one or more of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, or a chaotropic agent.

Cyclodextrins can be, but are not limited to, α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl α-cyclodextrin, (2,3,6-tri-O-benzoyl)-β-cyclodextrin, succinyl-(2-hydroxypropyl)-β-cyclodextrin, or succinyl-(2-hydroxypropyl)-γ-cyclodextrin. Cyclodextrins can also be a cyclodextrin polymer containing one or more of the foregoing cyclodextrin molecules. Additional cyclodextrins are known in the art, and include, e.g. those described on the world wide web at cyclodextrin.com. Exemplary concentrations of cyclodextrins are, without limitation, about 1 mM, 2 mM, 2.5 mM, 5 mM, 7.5 mM, 10 mM, 15 mM, 20 mM, 25 mM, 50 mM, 75 mM, or 100 mM.

Non-ionic surfactants can be polyethylene-sorbitan-fatty acid esters, polyethylene-polypropylene glycols or polyoxyethylene-stearates. Polyethylene-sorbitan-fatty acid esters can be polyethylene(20)-sorbitan-esters (Tween 20™) or polyoxyethylene(20)-sorbitanmonooleate (Tween 80™). Polyethylene-polypropylene glycols can be polyoxypropylene-polyoxyethylene block co-polymers such as those sold under the names Pluronic® or Poloxamer™ Polyoxyethylene-stearates can be, for example, those sold under the trademark Myrj™ Exemplary, polyoxyethylene monolauryl ethers include those sold under the trademark Brij™ e.g., Brij-35. Exemplary concentrations of non-ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Ionic surfactants can be anionic surfactants or cationic surfactants. Anionic surfactants useful in the present invention can be, but are not limited to, soaps including alkali soaps, such as sodium, potassium or ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride or quarternary ammonium compounds such as benzalkonium chloride. Ionic surfactants can include the sodium, potassium or ammonium salts of alkyl sulfates, such as sodium dodecyl sulfate or sodium octyl sulfate. Exemplary concentrations of ionic surfactants are, without limitation, about 0.01%, 0.02%, 0.05%, 0.1%, 0.2%, 0.5%, 0.75%, 1%, 2%, 2.5%, 5%, 7.5%, or about 10% w/w, w/v, or v/v.

Zwitterionic surfactants have both cationic and anionic centers attached to the same molecule. The cationic part is, e.g., based on primary, secondary, or tertiary amines or quaternary ammonium cations. The anionic part can be a sulfonate, as in CHAPS (3-[(3-Cholamidopropyl)dimethylammonio]-1-propanesulfonate). Other anionic groups are sultaines illustrated by cocamidopropyl hydroxysultaine or betaines, e.g., cocamidoethyl betaine, cocamidopropyl betaine, or lauramidopropyl betaine. Exemplary concentrations of zwitterionic surfactants are, without limitation, about 0.01%, 0.02%, 0.05%, 0.1%, 0.2%, 0.5%, 0.75%, 1%, 2%, 2.5%, 5%, 7.5%, and about 10% w/w, w/v, or v/v.

Non detergent sulfobetaines (NDSBs) have a sulfobetaine hydrophilic group and a short hydrophobic group that cannot aggregate to form micelles, therefore NDSBs are not considered detergents. Exemplary NDSBs include, but are not limited to NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, or Dimethylethylammoniumpropane sulfonate. Exemplary concentrations of NDSBs include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Polyols are compounds with multiple hydroxyl functional groups. In some cases, polyols can modify the aggregation or denaturation behavior of a protein by a variety of mechanisms. For example, in some cases, the polyol can shift the equilibrium to the folded state by presenting a thermodynamically disfavored interaction with the protein backbone. Alternatively, in some cases, the polyol can bind to and stabilize the folded state of the protein.

Polyols can be simple sugars such as sucrose, mannitol, sorbitol, inositol, xylitol, erythritol, glucose, galactose, raffinose, or trehalose. Polyols can also be polysaccharides such as dextran, starch, hydroxyethyl starch, or polymers containing one or more of the simple sugars described herein. Glycerol, ethylene glycol, polyethylene glycol, pentaerythritol propoxylate, and pentaerythritol propoxylate, and combinations thereof are also exemplary polyols.

Organic solvents can be, but are not limited to, those organic solvent that are known to inhibit denaturation, unfolding, or aggregation of one or more proteins. A variety of suitable organic solvents are known in the art. For example, organic solvents can include ethanol, butanol, propanol, phenol, dimethyl formamide, 2-methyl-2,4-pentanediol, 2,3-butanediol, 1,2-propanediol, 1,6-hexanediol, or dimethyl sulfoxide.

Aggregation modifying proteins can be proteins known in the art to inhibit denaturation, unfolding, or aggregation of one or more proteins. Exemplary aggregation modifying proteins include, but are not limited to, albumins, protein chaperones, and heat shock proteins. Albumins are proteins that are water-soluble, are moderately soluble in concentrated salt solutions, and experience heat denaturation. Exemplary albumins include serum albumins (e.g., bovine, horse, or human serum albumin) or egg albumin (e.g., hen egg-white albumin). Other exemplary aggregation modifying proteins include casein, gelatin, ubiquitin, lysozyme, or late embryogenesis abundant (LEA) proteins. LEA proteins include LEA I, LEA II, LEA III, LEA IV, LEA V, or atypical LEA proteins. LEA proteins are known in the art and described, e.g., in Goyal K., et al., Biochemical Journal 288(pt. 1), 151-57, (2005).

Protein aggregation modifying agents can also be amino acids. In some cases, the amino acids can serve an oxidoreduction function to maintain an appropriate oxidative potential for the protein immobilized on the substrate 112. Suitable oxido-reductive amino acids include cysteine and cystine. Other amino acids serve to reduce denaturation or aggregation through a non-oxido-reductive method. For example, arginine, glycine, proline, and taurine have been shown to reduce protein aggregation.

Other oxido-reduction agents can be employed to reduce protein aggregation. Oxido-reductants other than cysteine and cystine, can be used to optimize the reduction potential in the substrate 112 onto which the protein is immobilized. Exemplary oxido-reductants include mercaptoethanol, dithiothreitol, dithioerythritol, tris(2-carboxyethyl)phosphine, glutathione, glutathione disulfide, and oxidized derivatives thereof, as well as $Cu^{2+}$.

Protein aggregation modifying agents can also include lyoprotectants, cryoprotectants, or chaotropic agents. In some cases, the protein aggregation modifying agent is a chaotrope such as urea, thiourea, guanidinium, cyanate, thiocyanate, trimethylammonium, tetramethylammonium, cesium, rubidium, nitrate, acetate, iodide, bromide, trichloroacetate, or perchlorate. Under certain conditions, such as at low concentrations, chaotropes can reduce protein aggregation. Other protein aggregation modifying agents include trimethylamine N-oxide.

Protein aggregation modifying agents can be salts. Exemplary salts include, but not limited to, the sodium, potassium, magnesium, or calcium salts of chloride, sulfate, or phosphate. Protein aggregation modifying agents can also be buffering agents. Exemplary buffering agents include, but are not limited to, tris(hydroxymethyl)amino methene (TRIS), TAPSO, IVIES, HEPES, PIPES, CAPS, CAPSO, MOPS, MOPSO, or sodium or potassium phosphate, carbonate, bicarbonate, citrate, acetate, or borate buffers.

The protein aggregation modifying agents can be provided in any suitable concentration. In some cases, the protein is provided as an aqueous solution containing binding reagent and protein aggregation modifying agents. In such cases, the solution can be contacted with a reagent layer and, optionally, dried. Exemplary concentrations of protein aggregation modifying agents in the aqueous binding reagent solution include, but are not limited to, about 0.001%, 0.005%, 0.01%, 0.05%, 0.1%, 0.5%, 1%, 2%, 4%, 5%, 10%, 20%, or about 25% or more w/v of the solution. Further exemplary concentrations include, but are not limited to, about 1 µM, 5 µM, 10 µM, 25 µM, 50 µM, 75 µM, 100 µM, 150 µM, 200 µM, 300 µM, 500 µM, 750 µM, 1 mM, 5 mM, 10 mM, 25 mM, 50 mM, 100 mM, 150 mM, 200 mM, 300 mM, 500 mM, and 1M.

In some cases, the protein aggregation modifying agents are provided on the reagent layer. Exemplary compositions containing a protein aggregation modifying agent and a reagent layer that contains about 0.001%, 0.005%, 0.01%, 0.05%, 0.1%, 0.5%, 1%, 2%, 3%, 4%, 5%, or about 10%, 20%, or about 25% by weight of one or more protein aggregation modifying agents.

Protein aggregation modifying agents can be provided in any suitable combination. For example, in some cases, 1, 2, 3, 4, 5, 6, 7, 8, 9, 10 or more of the foregoing protein aggregation modifying agents can be utilized to reduce aggregation of a binding reagent reversibly immobilized on a reagent layer. In some cases, prior to contacting the reagent layer with the binding reagent solution, the reagent layer contains a protein aggregation modifying agent, and the binding reagent solution contains the same, or a different, protein aggregation modifying agent. In some cases, prior to contacting the reagent layer with the binding reagent solution, the reagent layer contains a protein aggregation modifying agent, and the binding reagent solution does not contain a protein aggregation modifying agent. In some cases, prior to contacting the reagent layer with the binding reagent solution, the binding reagent solution contains a protein aggregation modifying agent and the reagent layer, or the region to be contacted, does not.

Methods

A method of performing a lateral flow western blot assay using the lateral flow devices depicted in FIGS. 1-3 and 5 will now be described. The method begins by placing the substrate 112, 412 face down onto (e.g., in intimate contact with) the wicking pad 102, which can be supplied pre-moistened or can be pre-moistened by the user with, for example, running buffer. In some embodiments, the substrate 112, 412 is placed on the wicking pad 102, 402 downstream from the first reservoir 114, 214, 314, 414 and upstream from the second reservoir 116, 416 (e.g., between the first reservoir and the second reservoir).

The first reservoir 114, 214, 314, 414 is then formed by stacking one or more reagent layers 118, 218, 318, 418 (e.g., primary antibody, first wash solution, secondary antibodies or secondary detection reagents, second wash solution) on a first end 104, 404 of the wicking pad 102, 402. In embodiments in which the reagent layers are formed from absorbent material (FIGS. 1-2B, 5), the reagent layers 118, 418 are stacked dry or pre-moistened (by the user or the supplier) with a reagent-containing solution or with running buffer (e.g., for reagent layers having dry embedded reagents). In embodiments in which reagent layers 118, 418 are stacked dry, running buffer can be applied to the first reservoir 114, 414 after stacking the dry reagent layers 118, 418. In embodiments in which the reagent layers 218, 318 are solutions (FIGS. 3 and 4A), the solutions are stacked in a container (e.g., in a cylinder or trough). In some embodiments, the stack of reagent layers 118, 218, 318, 418 starting with the layer in contact with (FIGS. 1-2B) or closest to (FIGS. 3-4A) the wicking pad 102, 402, includes a first reagent layer having labeled primary antibody and a second reagent layer having a first wash solution. In certain embodiments, the stack of reagent layers 118, 218, 318, 418 is formed in the following order: a first reagent layer having primary antibody, a second reagent layer having a first wash solution, a third reagent layer having a secondary antibody or a secondary detection reagent, and a fourth reagent layer having a second wash solution. In some embodiments, the stack of reagent layers includes two or more layers (or twice the volume) of the same reagent. In some embodiments, a fifth reagent layer having the second wash solution (e.g., a second layer of the second wash solution) is included such that the first reservoir has twice the volume of the second wash solution. In some embodiments, the reagent layers having the second wash solution are omitted to allow the secondary antibody or secondary detection reagent more time to bind to the primary antibody.

In embodiments having reagent immobilized in absorbent reagent layers 118, 418, to initiate sequential flow of the reagents from the first reservoir 114, 414 to the wicking pad 102, 402, running buffer is applied to the absorbent reagent layers 118, 418 in the first reservoir 114, 414. Alternatively, liquid in the pre-wetted reagent layers is allowed to flow into the wicking pad 102, 402. In embodiments in which the reagent layers 218, 318 are in the form of solutions (FIGS. 3-4C), the solutions are allowed to flow sequentially from the first reservoir 214, 314 onto the first end 104 of the wicking pad 102 or into one or more dry or pre-moistened absorbent pads on the first end 104 of the wicking pad 102.

Figure 4B:
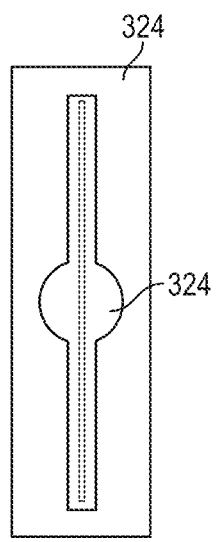
Figure 4C:
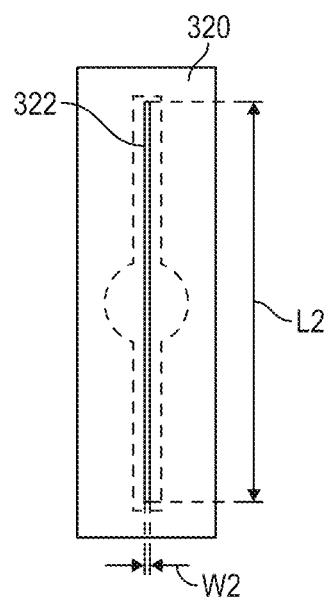

In embodiments having a valve 222 on a first end 220 of the first reservoir 214, the valve 222 is opened to allow the solutions to exit the first reservoir 214 (FIG. 3). In certain embodiments, the solutions are allowed to flow from a slit 322 on a first end 320 of the first reservoir 314 (FIGS. 4A-4C). In embodiments having a slit 322 on the first end 320 of the first reservoir 314, the slit is sealed with a removable metal foil or plastic foil (e.g., tape) prior to filling the first reservoir 314 with the reagent solutions and then the foil is removed to initiate flow of the solutions out of the first reservoir 314. In embodiments in which the first reservoir 314 has a reversibly sealed opening 324 on a second (top) end 324, flow of solutions is initiated by removing or puncturing the seal (e.g., metal or plastic seal) before or concurrent with removal of the foil covering the slit 322.

The running buffer or solutions are pulled by wicking from the first reservoir 114, 414 to the dry second reservoir 116, 416, carrying the reagents (e.g., the primary antibody, the first wash solution, and if needed, secondary antibodies and the second wash solution) sequentially by lateral flow into contact with the substrate 112, 412 having proteins immobilized thereon. In some embodiments (FIG. 5), the reagents follow a sinuous path 442 as they flow through the first reservoir 414 and into the wicking pad 402. The primary antibodies in the first reagent layer are transported in the wicking pad 102, 402, contact the proteins on the substrate 112, 412, and bind to the target proteins, if present, on the substrate 112, 412. In some embodiments, lateral flow of the running buffer/solutions from the first reservoir 114, 214, 314, 414 to the second reservoir 116, 416 further allows the first wash solution in the second reagent layer to be transported in the wicking pad 102, 402 such that unbound primary antibodies are removed from the substrate 112, 412. In certain embodiments, lateral flow of the running buffer/solutions from the first reservoir 114, 214, 314, 414 to the second reservoir 116, 416 further allows the secondary antibodies or a secondary detection reagent in a third reagent layer to be transported in the wicking pad 102, 402 and to contact the primary antibodies bound to their target proteins, if present, on the substrate 112, 412. In some embodiments, lateral flow of the running buffer/solutions from the first reservoir 114, 214, 314, 414 to the second reservoir 116, 416 further allows the second wash solution in the fourth reagent layer to be transported in the wicking pad 102, 402 such that unbound secondary antibodies are removed from the substrate 112. In some embodiments, the volume of the second wash solution applied to and transported in the wicking pad 102, 402 is twice the volume of secondary antibody applied to and transported in the wicking pad 102, 402.

In some embodiments, after initiating and/or during lateral flow, a substantially uniform pressure is applied to the first reservoir 114, 314, 414 and, optionally, to the second reservoir 116, 416 to improve contact of the first reservoir or both the first and second reservoirs with the wicking pad 102, 402. For example, a weight can be placed on top of one or both reservoirs to urge one or both reservoirs toward the wicking pad 102, 402.

In some embodiments, during lateral flow, the binding of primary antibodies to the target proteins (and optionally contact of secondary antibodies or secondary detection reagents to the primary antibody) is followed visually or by using a detector. In some embodiments, the substrate 112, 412 is removed from the lateral flow device and the binding of the primary antibodies to the target proteins, if present, is detected. In some embodiments, the antibody binding to the target protein is visualized and/or detected through the use of detectable moieties and/or labels as described herein. Suitable labels and/or moieties are detected by spectroscopic, photochemical, biochemical, immunochemical, isotopic, electrical, optical, chemical, or mass spectrometric techniques.

Generally, if the device is supplied in a case, the lid or cover will be placed back onto the device once the reagent layers have been applied to the wicking pad 102 to minimize evaporation and to apply even pressure to the first and second reservoirs 114, 116. The cover can be snap-fit onto the base of the case to apply even pressure or the cover can be placed loosely on top of the base and then the base with the cover can be placed into a drawer-like container that slides into a box. Prior to attaching the cover or in place of the cover, a sponge can be placed on the first and second reservoirs to aide in applying even pressure to the reservoirs. The entire process requires minimal user interaction with the consumable.

There are many absorbent bibulous pad materials, wick pad materials, and antibody application materials known in the art, the selection from which can be made to control the volume, to control the flow rate of the system, to ensure even flow, and to ensure complete delivery of antibodies/reagents from the first reservoir. Other methods that affect the timing of reagent/antibody delivery such as using torturous paths in the wick pad or controlling the contact area of the absorbent pad having immobilized antibody and, hence, the rate of antibody removal are possible. Still other embodiments to control the lateral flow process could be engineered into the plastic casing where the surface may contain sloped regions to slow or speed the flow of liquid using gravity.

Shown in FIGS. 2A and 2B is a consumable device that holds a single mini-gel sized membrane. Often users run western blots using membranes termed midi size blots which are typically 2× the width of a mini sized membrane. In other western blot applications the user may cut a mini and/or midi sized membrane into smaller sections that correspond to a few lanes of the original gel used for electrophoresis and transfer of the proteins. Therefore, the consumable lateral flow device 100 could be of a size to accommodate either a mini or midi-sized membrane in some embodiments. In still other embodiments there could be separate ridges molded into or otherwise present in the base of the consumable where membrane sections could be placed. In this later setup up, smaller first reservoirs loaded with different antibodies may be placed at the head of each section to facilitate western blot probing of each section of membrane with a different antibody in the same device.

In other embodiments of this western blot lateral flow device, antibodies may be mixed and loaded into a first reagent layer in the first reservoir to facilitate multiplex detection of targets in a single sample.

IV. KITS

Kits for performing a lateral flow western blot assay according to methods described herein are provided. Also provided are kits containing devices as described herein. In some embodiments, a kit comprises a first reservoir comprising a stack of a plurality of reagent layers located on a first end of a wicking pad and a second reservoir comprising an absorbent pad located on a second end of the wicking pad, all of which are described herein. In some embodiments, the kit comprises reagents (e.g., binding reagents including labeled primary antibody or primary and secondary antibodies, wash solution, and/or running buffer) in liquid form. In some embodiments, the kit contains one or more absorbent reagent layers each with a reagent reversibly bound therein. In certain embodiments, some or all of the reagents are dried onto an absorbent reagent layer. In some embodiments, some or all of the reagents are dried onto an absorbent reagent layer, or portion thereof, in the presence of one or more protein aggregation modifying agents. In some embodiment, the reagents are provided as solutions to be applied to the absorbent reagent layers by the end-user. In some cases the solutions for each reagent may be of different density to minimize mixing of different reagents. In some embodiments, a float as described in U.S. Pat. No. 6,641,517 may be provided for use with a cylinder or trough to minimize mixing of the reagents while solutions having different densities are stacked. An exemplary embodiment of a float 326 is illustrated in FIG. 4A.

In some embodiments, the kit includes a plastic tray with two, four, or more quadrants for the user to apply reagent solutions to the absorbent pads prior to forming a stack of reagent layers 118.

In some embodiments, the kit contains running buffer and/or blocking agents (e.g., bovine serum albumin and/or non-fat dried milk), surfactants (e.g., Tween 20 or Triton X-100), protein aggregation modifying agents as described herein, crowding agents (e.g., dextran, polyethylene glycol and/or Ficoll), and/or agents to promote even flow of reagents and/or promote reaction to molecules on the substrate and minimize background on the substrate. The additional agents can be provided in the kit as a solid (e.g., a powder) or in liquid form (e.g., as a solution). In some embodiments, the kit further comprises instructions for carrying out the methods described herein.

IV. EXAMPLES

These examples illustrate the use of a lateral flow device as depicted in FIGS. 1-2B and as described herein to perform western blot assays.

Example 1

Detection of Tubulin and GAPDH from HEK293 Cell Lysate Using Different Dilutions of Secondary Antibody Lyophilized HEK293 protein lysate (Bio-Rad Laboratories PrecisionAb control lysate VLY001) was reconstituted in 1× Laemmli sample buffer containing 40 mM DTT and denatured by heating at 100° C. for 5 min. A series of two-fold dilutions of the lysate (20 ug down to 0.04 ug) was loaded onto 4-20% TGX mini gels (Bio-Rad Laboratories) and electrophoresed at 250V for 25 min. Each gel was transferred to a PVDF membrane using the Transblot Turbo device and prepacked transfer pack using a setting of 1.3 A×7 min. Following transfer, the membranes were quickly rinsed in 1× PBS buffer and then placed in a lateral flow buffer containing 1% casein, 1×PBS Buffer, 0.1% Tween 20, and placed on a rocker for 10 minutes to block. While the membranes were incubating in lateral flow buffer, primary antibody was prepared by mixing 5 µl each of rabbit anti-tubulin polyclonal Ab (Cell signaling Technologies #2148) and rabbit anti-GAPDH mAb (Cell Signaling Technologies #5174) antibodies into 5 ml of lateral flow buffer. Secondary antibody (goat anti-rabbit IgG-HRP antibody conjugate, Cell Signaling Technologies #7074) was prepared at three different dilutions (1:1000, 1:5000 and 1:10000) in lateral flow buffer. A separate tray with 4 chambers of ~2.5×10 cm was used to wet the reagent layers with antibodies and wash solutions. The following solutions were pipetted into the chambers: 4.5 ml of primary antibody into chamber 1, 4.5 ml of lateral flow buffer into chamber 2 (wash1), 4.5 ml of secondary antibody into chamber 3, and 27 ml lateral flow buffer into chamber 4 which contained a stack of 30 layers of transblot turbo pad material (wash2). A sheet of blot paper was added to each of chambers 1 to 3 to completely absorb the solution to reversibly immobilize the reagent in the blot paper.

Figures 6A, 6B, 6C:
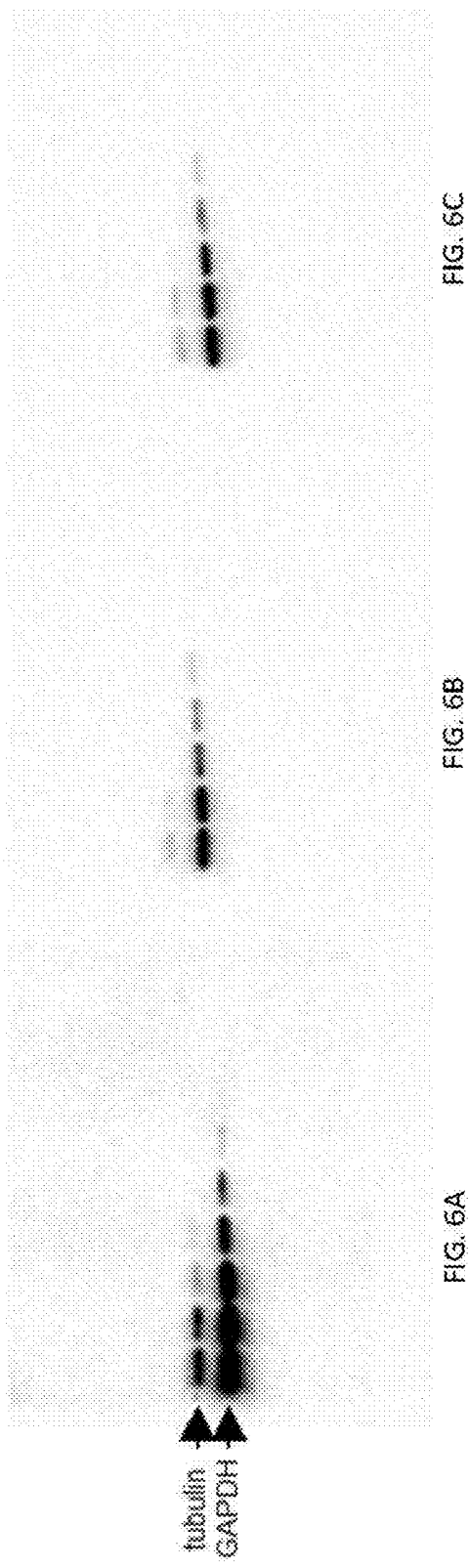

Blot detection was performed as follows. A paper wick pad (1CHR paper from GE Healthcare) was cut to 8.7 cm×18.7 cm and placed into the bottom of a vacuum molded tray as shown in FIG. 2A. Nine layers of thick blot paper about 4 cm×9.5 cm (Bio-Rad) were placed on one end of the wick pad to serve as the pump. The paper wick was wet with 3.5 ml of lateral flow buffer and rolled to remove bubbles. The membrane was removed from blocking and placed inverted (antigen side down) onto the wick pad with the low molecular weight proteins nearest the pump; bubbles were removed by rolling. One layer each of the blot papers containing absorbed primary Antibody, wash1 solution, secondary antibody and wash2 solution, respectively, were stacked on the end of the wick pad opposite the pump with the primary antibody layer contacting the wick pad (i.e., with the primary antibody layer being the first (or bottom) layer in the stack of reagent layers). A sponge of similar size to the wicking pad was placed on top of the antibody/buffer reservoir stack and pump. A plastic cover was placed on top of the sponge and the cover was clamped to the bottom tray using binder clips. A separate device was used for testing each of the three different dilutions of secondary antibody. The devices were left on a level surface at room temperature undisturbed. After 5 hours, the membranes were removed from the devices and washed 1×5 min in 1×PBS. Detection was then performed using Clarity chemiluminescent substrate (Bio-Rad Laboratories) per the instructions. FIGS. 6A, 6B and 6C are images of the three blot membranes corresponding to a 1:1000, a 1:5000, and a 1:10000 dilution, respectively, of secondary antibody. The images were taken from an 8 second exposure of the blots using Bio-Rad's ChemidocMP imager. The images show that both target antigens were detected at all three dilutions of secondary antibody.

Example 2

Detection of PCNA Antigen in HEK293 Lysate on PVDF and Nitrocellulose Membranes

Figures 7A, 7B:
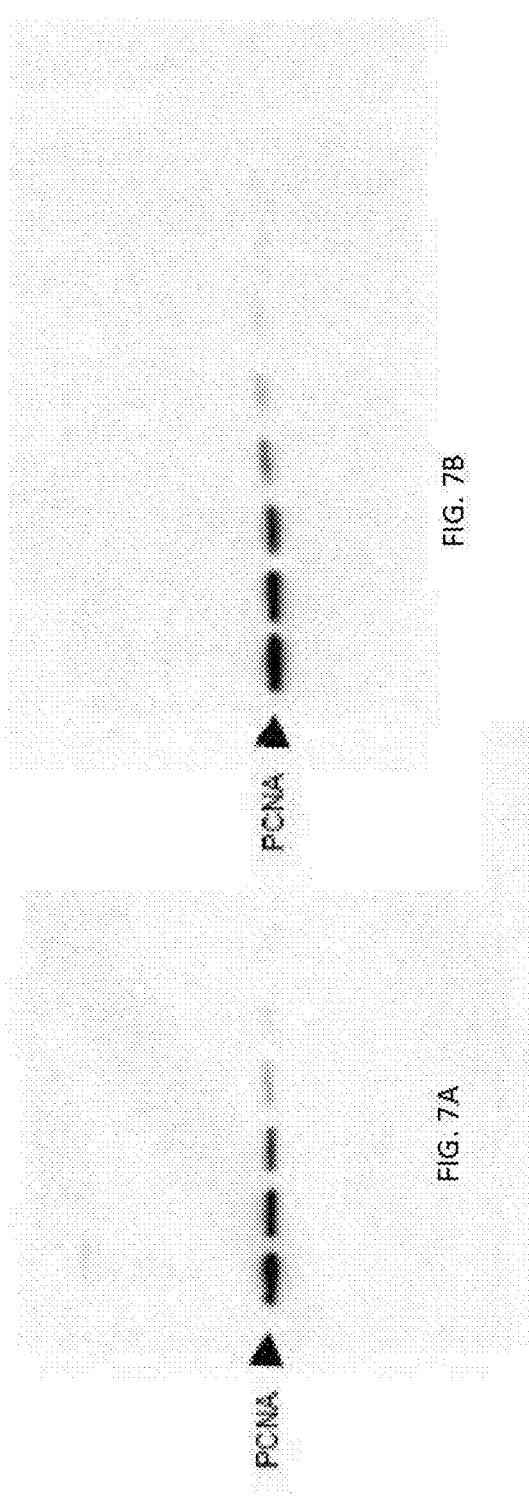

Conditions were as described in Example 1. Primary antibody was mouse anti-PCNA mAb (Bio-Rad Laboratories, #VMA00018) at 1:1000 dilution in lateral flow buffer. Secondary antibody was goat anti-mouse IgG-HRP conjugate (Bio-Rad Laboratories, #STAR207P) at 1:1000 dilution in lateral flow buffer. Images of the blots (see FIGS. 7A and 7B) were taken from a 0.7 second exposure using the ChemidocMP imager. The images show that the target antigen was detected at multiple dilutions on both types of membrane material, with the PVDF showing better sensitivity than the nitrocellulose.

Example 3

Detection of GSK3a/b Antigen in HEK293 Lysate on PVDF Membrane

Figure 8:
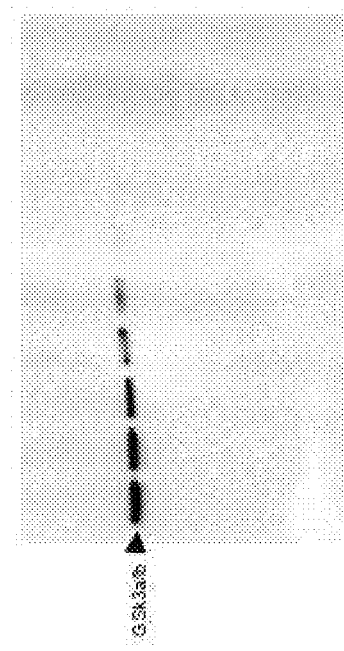

Conditions were as described in Example 1. Primary antibody was mouse anti-GSK3a/b mAb (Bio-Rad Laboratories, #VMA00342) at 1:1000 dilution in lateral flow buffer. Secondary antibody was goat anti-mouse IgG-HRP conjugate (Bio-Rad Laboratories, #STAR207P) at 1:1000 dilution in lateral flow buffer. The image shown in FIG. 8 was taken from a 2 second exposure of the blot using the ChemidocMP imager. The image shows that the target antigen was detected at multiple dilutions.

Example 4

Detection of PARP Antigen in HEK293 Lysate on PVDF Membrane

Figure 9:
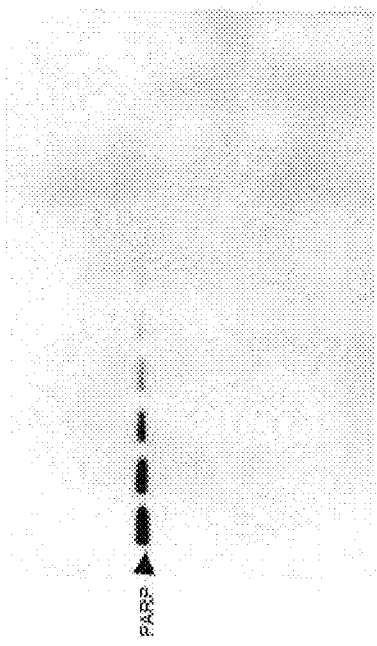

Conditions were as described in Example 1. Primary antibody was mouse anti-PARP mAb (Bio-Rad Laboratories, #VMA00016) at 1:1000 dilution in lateral flow buffer. Secondary antibody was goat anti-mouse IgG-HRP conjugate (Bio-Rad Laboratories, #STAR207P) at 1:1000 dilution in lateral flow buffer. The image shown in FIG. 9 was taken from a 6 second exposure of the blot using the ChemidocMP imager. The image shows that the target antigen was detected at multiple dilutions.

Example 5

Detection of hRAS Antigen in HEK293 Lysate on PVDF Membrane

Figure 10:
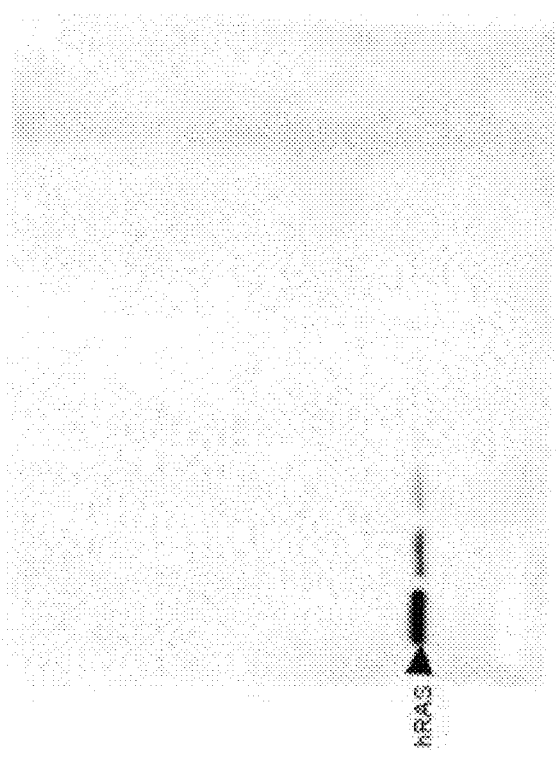

Conditions were as described in Example 1. Primary antibody was mouse anti-hRAS (Bio-Rad Laboratories, #VMA00040) at 1:1000 dilution in lateral flow buffer. Secondary antibody was goat anti-mouse IgG-HRP conjugate (Bio-Rad Laboratories, #STAR207P) at 1:1000 dilution in lateral flow buffer. The image shown in FIG. 10 was taken from a 12 second exposure of the blot using the ChemidocMP imager. The image shows that the target antigen was detected at multiple dilutions.

Examples 1-5 illustrate that the lateral flow devices described herein can deliver western blotting reagents (e.g., specific binding reagents, running buffer, wash solutions) sequentially and without user intervention to a blot on a wicking pad.

All patents, patent applications, and other published reference materials cited in this specification are hereby incorporated herein by reference in their entirety.

What is claimed is:

1. A lateral flow device comprising:
   a wicking pad composed of a porous material, the wicking pad having a region for applying a substrate comprising immobilized analytes; and
      wherein the wicking pad has a first end, a second end and two lateral edges;
   a first reservoir comprising a stack of a plurality of reagent layers located on the first end of the wicking pad; and
   a second reservoir comprising an absorbent pad located on the second end of the wicking pad.

2. The device of claim 1, wherein each of the plurality of reagent layers comprises a reagent immobilized in an absorbent pad.

3. The device of claim 2, wherein each of the plurality of reagent layers has a different reagent therein.

4. The device of claim 2, wherein the reagent is selected from the group consisting of a primary antibody, a secondary antibody, a first wash solution, and a second wash solution.

5. The device of claim 1, wherein the plurality of reagent layers, starting at a reagent layer in contact with the wicking pad, comprises a first reagent layer having a primary antibody, a second reagent layer having a first wash solution, a third reagent layer having a secondary antibody, and a fourth reagent layer having a second wash solution.

6. The device of claim 5, wherein the fourth reagent layer is at least twice the thickness of the third reagent layer.

7. The device of claim 5, further comprising a fifth reagent layer comprising the second wash solution.

8. The device of claim 5, wherein the volume of the second wash solution is at least twice the volume of the secondary antibody.

9. The device of claim 5, wherein each of the plurality of reagent layers is formed of an absorbent pad and at least a portion of the first reagent layer is in intimate contact with the wicking pad.

10. The device of claim 1, wherein the analytes are proteins.

11. The device of claim 1, wherein the device is sealed in a plastic casing.

12. The device of claim 11, wherein the plastic casing comprises a molded bottom portion and a planar cover sealed to the bottom portion.

13. The device of claim 1, wherein the wicking pad and reservoirs are dry.

14. The device of claim 1, wherein at least one of the wicking pad and the first reservoir is wet.

15. The device of claim 1, wherein the reagent layers are each formed of at least one absorbent material selected from the group consisting of cotton, glass fiber, cellulose, a cellulose fiber derivative, sintered glass, sintered polymer, sintered metal, and a synthetic polymer.

16. The device of claim 15, wherein the synthetic polymer is selected from the group consisting of polyacrylamide, nylon, polypropylene, polyethylene, polystyrene, divinylbenzene, polyvinyl, polyvinyl difluoride, high density polyvinyl difluoride, a ($C_2$-$C_6$) monoolefin polymer, a vinylaromatic polymer, a vinylaminoaromatic polymer, a vinylhalide polymer, a ($C_1$-$C_6$) alkyl (meth)acrylate polymer, a(meth)acrylamide polymer, a vinyl pyrrolidone polymer, a vinyl pyridine polymer, a ($C_1$-$C_6$) hydroxyalkyl (meth)acrylate polymer, a (meth)acrylic acid polymer, an acrylamidomethylpropylsulfonic acid polymer, an N-hydroxy-containing ($C_1$-$C_6$) alkyl(meth)acrylamide polymer, and acrylonitrile.

17. The device of claim 1, wherein each of the reagent layers further comprises a barrier layer on a portion of a lower surface.

18. A kit for lateral flow, the kit comprising,
    the device of claim 1.

19. A method of performing a lateral flow assay, the method comprising:
    providing the device of claim 1;
    applying a running buffer to the wicking pad;
    applying a substrate comprising proteins to the region for applying the substrate comprising analytes;
    optionally wetting the first reservoir with the running buffer; and
    allowing lateral flow of the running buffer from the first reservoir to the second reservoir such that reagents in the plurality of reagent layers are sequentially transported in the wicking pad and are contacted to the proteins on the substrate.

20. The method of claim 19, wherein the allowing lateral flow step comprises allowing primary antibodies from a first reagent layer to bind to their target proteins, if present, on the substrate, followed by allowing a first wash solution from a second reagent layer to remove unbound primary antibodies from the substrate.

21. The method of claim 20, wherein the allowing lateral flow step further comprises allowing secondary antibodies or a secondary detection reagent from a third reagent layer to contact the primary antibodies bound to their target proteins, if present, on the substrate.

22. The method of claim 21, wherein the allowing lateral flow step further comprises allowing a second wash solution from a fourth reagent layer to remove unbound secondary antibodies from the substrate.

23. The method of claim 19, further comprising applying a substantially uniform pressure to the first reservoir and the second reservoir.

24. The method of claim 19, further comprising following binding of the primary antibodies to the target proteins, if present, (and optionally contact of secondary antibodies or secondary detection reagents to the primary antibodies), removing the substrate, and detecting the binding of the primary antibodies to the target proteins if present.

25. The method of claim 19, wherein the allowing lateral flow step comprises allowing the reagents to follow a sinuous path as they flow through the first reservoir and into the wicking pad.

* * * * *